US009241927B2

(12) United States Patent
Soler Ranzani et al.

(10) Patent No.: US 9,241,927 B2
(45) Date of Patent: Jan. 26, 2016

(54) PHARMACEUTICAL COMPOSITIONS COMPRISING SIGMA RECEPTOR LIGANDS (75) Inventors: Luis Soler Ranzani, Barcelona (ES); Pierandrea Esposito, Barcelona (ES); Gemma Casadevall Pujals, Barcelona (ES); Nuria Cubel Suñé, Barcelona (ES)

(73) Assignee: Laboratories Del Dr, Esteve, S.A., Barcelona (ES)

( * ) Notice: Subject to any disclaimer, the term of this patent is extended or adjusted under 35 U.S.C. 154(b) by 0 days.

(21) Appl. No.: 13/511,706

(22) PCT Filed: Nov. 25, 2010

(86) PCT No.: PCT/EP2010/068213
§ 371 (c)(1),
(2), (4) Date: Jul. 25, 2012

(87) PCT Pub. No.: WO2011/064296
PCT Pub. Date: Jun. 3, 2011

(65) Prior Publication Data
US 2012/0283262 A1   Nov. 8, 2012

(30) Foreign Application Priority Data

Nov. 25, 2009   (EP) .................................... 09382261

(51) Int. Cl.
*A61K 31/4152*   (2006.01)
*A61K 9/16*   (2006.01)

(52) U.S. Cl.
CPC ........... *A61K 31/4152* (2013.01); *A61K 9/1623* (2013.01); *A61K 9/1652* (2013.01); *A61K 9/1694* (2013.01)

(58) Field of Classification Search
CPC ............ A61K 31/415; A61K 31/4155; A61K 31/5375; C07D 265/28; C07D 265/30; C07D 231/22
See application file for complete search history.

(56) References Cited

FOREIGN PATENT DOCUMENTS

EP          2 116 539 A1    11/2009
WO     WO 2006/021462 A1    3/2006

OTHER PUBLICATIONS

Dukíc-Ott, A., "Production of pellets via extrusion-spheronisation without the incorporation of microcrystalline cellulose: a critical review", European Journal of Pharmaceutics and Biopharmaceutics, 2009, vol. 71, pp. 38-46.
Hileman, G.A. et al., "Response surface optimization of high dose pellets by extrusion and spheronization", International Journal of Pharmaceutics, 1993, vol. 100, pp. 71-79.
Jover, I. et al., "Evaluation, by a Statistically Designed Experiment, of an Experimental Grade of Microcrystalline Cellulose, Avicel 955, as a Technology to Aid to Production of Pellets with High Drug Loading", Journal of Pharmaceutical Sciences, 1996, vol. 85, No. 7, pp. 700-705.
Kranz, H. et al., "Drug Release from MCC- and carrageenan-based pellets: Experiment and theory", European Journal of Pharmaceutics and Biopharmaceutics, 2009, vol. 73, pp. 302-309.
Snyder, S.H. and Largent, B.L., "Receptor Mechanisms in Antipsychotic Drug Action: Focus on Sigma Receptors", Journal of Neuropsychiatry, 1989, vol. 1, No. 1, pp. 7-15.
Walker, J.M. et al., "Sigma Receptors: Biology and Function", Pharmacological Reviews, 1990, vol. 42, No. 4, pp. 355-402.
Extended European Search Report issued by the European Patent Office on Apr. 14, 2010 in connection with European Patent Application EP 09 38 2261.
International Search Report issued by the International Searching Authority (ISA/O.E.P.M.) on Mar. 15, 2011 in connection with International Application No. PCT/EP2010/068213.
Abadías, M. et al. "Saftey, Tolerability and Pharmacokinetics of Single and Multiple Doses of a Novel Sigma-1 Receptor Antagonist in Three Randomized Phase I Studies", British Journal of Clinical Pharmacology, 2012, 75:1, 103-117.
Laggner et al. "Discovery of High Affinity Ligands of Sigma-1 Receptor, ERG2, and Emopamil Binding Protein by Pharmacophore Modeling and Virtual Screening", J. Med. Chem, 2005, 48, 4754-4764.

*Primary Examiner* — Wu-Cheng Winston Shen
*Assistant Examiner* — Christopher R Stone
(74) *Attorney, Agent, or Firm* — Gary J. Gershik; Cooper & Dunham LLP (57) ABSTRACT The present invention relates to a pharmaceutical composition that comprises a compound of formula (I) as active pharmaceutical ingredient:

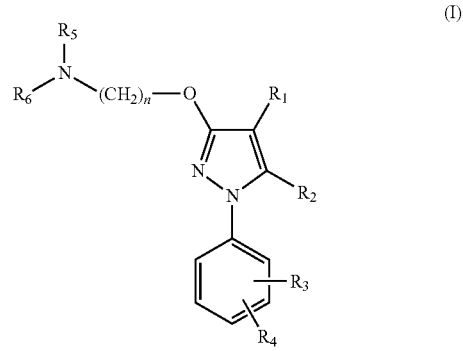

or a pharmaceutically acceptable salt, isomer, prodrug or solvate thereof; and at least a pharmaceutically acceptable excipient, wherein the active pharmaceutical ingredient is present in an amount of at least 80% of the total dry weight of the composition.

7 Claims, 2 Drawing Sheets

PHARMACEUTICAL COMPOSITIONS COMPRISING SIGMA RECEPTOR LIGANDS

This application is a §371 national stage application of PCT International Application No. PCT/EP2010/068213, filed Nov. 25, 2010, claiming priority of European Patent Application No. EP 09 382 261.7, filed Nov. 25, 2009, the contents of all of which are hereby incorporated by reference into this application.

FIELD OF THE INVENTION

The present invention relates to pharmaceutical compositions comprising a high load of compounds having pharmacological activity towards the sigma (σ) receptor, to their processes of preparation and uses thereof.

BACKGROUND OF THE INVENTION

The search for new therapeutic agents has been greatly aided in recent years by a better understanding of the structure of proteins and other biomolecules associated with target diseases. One important class of proteins is the sigma (σ) receptor, a cell surface receptor of the central nervous system (CNS) which may be related to the dysphoric, hallucinogenic and cardiac stimulant effects of opioids. From studies of the biology and function of sigma receptors, evidence has been presented that sigma receptor ligands may be useful in the treatment of psychosis and movement disorders such as dystonia and tardive dyskinesia, and motor disturbances associated with Huntington's chorea or Tourette's syndrome and in Parkinson's disease (Walker, J., et al, Pharmacol. Rev. 1990; 42:355). It has been reported that the known sigma receptor ligand rimcazole clinically shows effects in the treatment of psychosis (Snyder, S., Largent, B., J. Neuropsychiatry 1989; 1:7). The sigma binding sites have preferential affinity for the dextrorotatory isomers of certain opiate benzomorphans, such as (+)SKF 10047, (+)cyclazocine, and (+)pentazocine and also for some narcoleptics such as haloperidol. Several sigma receptor ligands are disclosed in the prior art.

Patent application WO 2006/021462 discloses a family of pyrazol derivatives which are particularly selective as inhibitors of the sigma receptor. Said derivatives show a pyrazol group which is characterized by the substitution, at position 3, with an alkoxy group bounded to a nitrogen atom. These compounds have displayed strong analgesic activity in the treatment and prevention of chronic and acute pain and, particularly, neuropathic pain.

However, compounds disclosed in WO 2006/021462 have shown poor rheological properties and poor compressibility characteristics. This makes difficult to formulate them, since mechanical operations are normally applied on the compositions comprising the active ingredient, and good compressibility and rheological properties facilitate the handling and manufacture of the formulation.

In addition, the preparation of formulations with high load of active ingredient is not without problems. Formulations typically contain more than 20% of excipients by weight of the total formulation. This is necessary for the successful production of forms such as pellets which involves several mechanical steps, and optionally the use of a binder (Hileman, G., et al, Int. J. Pharma. 1993; 100(1-3):71-79; Jover, I., et et al, J. Pharma. Sci. 1996; 85:700-705). In particular diluents, binders and plasticizers play an important role in the properties of the final product, such as plastic characteristics of the solid formulation, necessary to obtain particles with the desired shapes, uniform size and good handling and dissolution properties.

For example, it is believed that microcrystalline cellulose (MCC), a usual diluent, acts as a molecular sponge by holding water applied during the wet massing step until pressure is applied (by extrusion or spheronization forces) that causes the held water to be expressed to the particle surface. The water present at the surface of the particles acts as a lubricant, reducing the shear forces of extrusion and thus assisting in the formation of cylindrical extrudate from the wetted mass. The water remaining inside the extrudate acts as a plasticizer in that it allows the MCC to be less structurally rigid during spheronization.

Unfortunately, the need to use certain amounts of excipients, such as diluents, limits the active load in the final formulation.

In general, the prevention and treatment of pain require formulations that enable the fast delivery of the analgesic agent to the patient. In addition, the development of pain often demands that a high dosage of the analgesic agent be administered immediately after or before the pain onset. Most patients usually experience episodes of high intensity pain at this juncture. Consequently, there is a need in the art for better formulations of the compounds described in WO 2006/021462 that would also enable a higher load of the active ingredient.

SUMMARY OF THE INVENTION

The inventors have surprisingly found that the compounds of formula (I), despite their poor rheological and compressibility characteristics, can provide pharmaceutical formulations that allow a high load of active ingredient, above 80% of the total dry weight of the formulation, and still exhibit good pharmaceutical properties such as, for example, release rate, particle size, roundness or yields after sieving. This is unexpected, because the physical properties of the compounds of formula (I) would point the other way, namely to use a higher than usual amount of excipients, such as diluents or hinders, to compensate such properties and be able to obtain a formulation with the appropriate characteristics.

Therefore, in a first aspect the invention is directed to a pharmaceutical composition that comprises (i) a compound of formula (I) as active pharmaceutical ingredient:

wherein
  $R_1$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted non-aromatic heterocyclyl, substituted or unsubstituted aromatic heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;

$R_2$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;

$R_3$ and $R_4$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$C(O)R_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen, or together form, with the phenyl group to which they are attached, a fused substituted or unsubstituted aryl group, or a fused substituted or unsubstituted heterocyclyl group;

$R_9$ and $R_6$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —$COR_8$, —$C(O)OR_8$, —$C(O)NR_8R_9$, —$CH=NR_8$, —$CN$, —$OR_8$, —$OC(O)R_8$, —$S(O)_t$—$R_8$, —$NR_8R_9$, —$NR_8C(O)R_9$, —$NO_2$, —$N=CR_8R_9$, and halogen;

or together form, with the nitrogen atom to which they are attached, a substituted or unsubstituted heterocyclyl group;

n is 1, 2, 3, 4, 5, 6, 7 or 8;

t is 1, 2 or 3;

$R_8$ and $R_9$ are each independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, and halogen;

or a pharmaceutically acceptable salt, isomer, prodrug or solvate thereof;

and (ii) at least a pharmaceutically acceptable excipient, wherein the active pharmaceutical ingredient is present in an amount of at least 80% of the total dry weight of the composition.

According to a second aspect, the invention is directed to a process for the preparation of the pharmaceutical composition of the invention, which comprises an extrusion/spheronization or a melt granule process.

A third aspect is a composition prepared according to the present invention for its use as a medicament.

A fourth aspect is a composition of the invention for use in the treatment or prophylaxis of a sigma receptor mediated disease or condition. In a particular embodiment, the disease is selected from the group consisting of diarrhea; lipoprotein disorders; migraine; obesity; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive diskinesia; ischemic stroke; epilepsy; stroke; stress; cancer; psychotic conditions, in particular depression, anxiety or schizophrenia; inflammation; and autoimmune diseases. In another particular embodiment, the disease is pain, preferably neuropathic pain, inflammatory pain or other pain conditions involving allodynia and/or hyperalgesia.

DETAILED DESCRIPTION OF THE INVENTION

The pharmaceutical compositions of the invention comprise at least 80% in weight of a compound of formula (I), but unexpectedly, can be manufactured under standard pharmaceutical processes, and show good pharmaceutical properties.

According to a particular embodiment, the active pharmaceutical ingredient ("API") is present in an amount of at least 85% of the total dry weight of the composition.

In another embodiment the pharmaceutically acceptable excipients, preferably diluent or binder, is present in an amount of less than 15%, more preferably less than 10%, of the total dry weight of the composition.

In a further embodiment, the weight ratio of the API to the pharmaceutically acceptable excipients is between 4:1 to 40:1, preferably between 5:1 to 40:1, more preferably between 8:1 to 30:1.

The pharmaceutically acceptable excipient in the composition of the present invention can be a diluent, one or more compounds which are capable of densifying the active principle to give the desired mass. Preferred diluents are:

inorganic phosphates, such as calcium and sodium phosphates;

sugars, such as hydrated or anhydrous dextrose, sucrose, galactose, maltose, lactose;

polyols, such as sorbitol, xylitol, manitol;

natural polymers, including:

polysaccharides, such as dextrates, maltodextrin, pectin, carrageenan, chitosan;

cylcodextrin;
cellulose or cellulose derivatives, such as microcrystalline cellulose (e.g. Avicel®, such as Avicel® PH101, Avicel® PH102 or Avicel® PH105, Emcocel®, Vivacel®, Ming Tai® or Salka-Floc®), microfine cellulose, sodium carboxymethyl cellulose, hydroxypropyl methylcellulose, hydroxypropyl cellulose;
starch or starch derivatives, including pregelatinized starch (Starch 1500 or National 1551), sodium starch glycolate, maize starch, potato starch, rice starch, wheat starch.

The pharmaceutically acceptable excipient in the composition of the present invention can be a binder, one or more compounds which are capable of imparting cohesive qualities to the materials. Preferred binders are:
cellulose or cellulose derivatives, such as sodium carboxymethyl cellulose, ethyl cellulose, hydroxyethyl cellulose, hydroxypropyl methylcellulose, hydroxypropyl cellulose, methyl cellulose;
synthetic polymers, such as polyvinylpyrrolidone, polyethylene glycol, polyethylene glycol glyceride, polyethylene oxide;
acids, such as pectinic acid, citric acid, fumaric acid, tartaric acid;
waxy or lipidic excipients, such as hydrogenated castor oil, glycerol palmitostearate (Precirol AT05), glycerol esters of saturated fatty esters (Gelucire), glyceryl behenate (Compritol), glyceryl monostearate;
guar gum, xanthan gum, colloidal silicon dioxide.

In a particular embodiment, the composition of the invention comprises a diluent or binder selected from:
inorganic phosphates, such as calcium and sodium phosphates;
sugars, such as hydrated or anhydrous dextrose, sucrose, galactose, maltose, lactose;
polyols, such as sorbitol, xylitol, manitol;
natural polymers, including:
polysaccharides, such as dextrates, maltodextrin, pectin, carrageenan, chitosan;
cylcodextrins;
cellulose or cellulose derivatives, such as microcrystalline cellulose (e.g. Avicel®, such as Avicel® PH101, Avicel® PH102 or Avicel® PH105, Emcocel®, Vivacel®, Ming Tai® or Salka-Floc®), microfine cellulose, sodium carboxymethyl cellulose, hydroxypropyl methylcellulose, hydroxypropyl cellulose;
starch or starch derivatives, including pregelatinized starch (Starch 1500 or National 1551), sodium starch glycolate, maize starch, potato starch, rice starch, wheat starch;
synthetic polymers, such as polyvinylpyrrolidone, polyethylene glycol, polyethylene glycol glyceride, polyethylene oxide;
acids, such as pectinic acid, citric acid, fumaric acid, tartaric acid;
waxy or lipidic excipients, such as hydrogenated castor oil, glycerol palmitostearate (Precirol AT05), glycerol esters of saturated fatty esters (Gelucire), glyceryl behenate (Compritol), glyceryl monostearate;
guar gum, xanthan gum, colloidal silicon dioxide;
or mixtures thereof.

In a further embodiment, the composition of the invention comprises a diluent or binder selected from:
sugars, such as dextrose, sucrose, galactose, maltose, lactose; and
polymeric materials, including cellulose or cellulose derivatives, such as microcrystalline cellulose (e.g. Avicel®, such as Avicel® PH101, Avicel® PH102 or Avicel® PH105, Emcocel®, Vivacel®, Ming Tai® or Salka-Floc®), microfine cellulose, sodium carboxymethyl cellulose, hydroxypropyl methylcellulose, hydroxypropyl cellulose; starch or starch derivatives, such as pregelatinized starch (Starch 1500 or National 1551), sodium starch glycolate, maize starch, potato starch, rice starch, wheat starch; polyvinylpyrrolidone, polyethylene glycol, polyethylene glycol glyceride; or mixtures thereof.

In a particular embodiment, when polyethylene glycol is used in the formulation of the invention, it has preferably an average weight between 3000 and 9000, preferably between 5000 and 9000, more preferably between 7000 and 9000.

In another particular embodiment, the polyethylene glycol glyceride is preferably lauroyl polyoxylglyceride.

According to a particular embodiment, the diluent or hinder is selected from: lactose, preferably lactose hydrate; celluloses, preferably microcrystalline cellulose; starch; polyethylene glycol, preferably with an average weight between 7000 and 9000; and polyethylene glycol glyceride, preferably lauroyl polyoxylglyceride; or mixtures thereof.

In an embodiment the binder is selected from water, hydroxypropyl methyl cellulose, carboxyvinyl polymer, carmellose sodium (e.g. Ac-Di-Sol®), alpha starch, polyvinylpyrrolidone (e.g. Polyvidon® CL, Polyvidon® CL-M, Kollidon® CL. Polyplasdone® XL or Polyplasdone® XL-10), gum Arabic, gelatin, pullulan and the like.

In a preferred embodiment, the binder of the formulation is preferably selected from the group formed by water, alcohol solutions such as ethanol solutions, or self emulsifying systems. More preferably, the binder is water.

In a further embodiment, the composition of the invention comprises both a diluent and a binder as pharmaceutically acceptable excipients.

The compositions and the dosage forms of the invention may further comprise one or more additional excipients.

The term "excipient" has the same meaning as that given in the US Pharmacopoeia and National Formulary, i.e. any component, other than the active substance(s) intentionally added to the formulation of a dosage form. Exemplary excipients are disintegrants, which act by swelling and/or wicking, lubricants, plasticizers, binders, fillers, colorants, flavour masking agents, flavouring agents, stabilizers, foaming agents, sweeteners, pore-forming agents, acids (e.g. citric or tartaric acid), sodium chloride, a bicarbonate (e.g. sodium or potassium), sugars and alcohols. The amount of excipients that can be used will be limited, since at least 80% of the total dry of the composition will be constituted by the active ingredient(s). Some excipients can serve multiple purposes, e.g be a filler and a disintegrant at the same time.

As examples of flavour masking agents, water insoluble polymers such as ethyl cellulose, polymers insoluble in saliva and soluble in gastric fluid such as a copolymer of methyl methacrylate, butyl methacrylate, and diethylaminoethyl methacrylate, and the like can be used.

By the term 'disintegrant' it is understood a substance which, upon addition to a solid preparation, facilitates its break-up or disintegration after administration and permits the release of an active ingredient as efficiently as possible to allow for its rapid dissolution. As examples of disintegrating agents, starches such as corn starch and potato starch, partial alpha starch, sodium carboxymethyl starch, hydroxypropyl starch; carmellose, carmellose calcium, crosscarmellose sodium (e.g. Ac-Di-Sol®), polyvinyl alcohol, crospovidone, hydroxypropyl cellulose, crystalline cellulose (e.g. Avicel®, such as Avicel® PH101, Avicel® PH102 or Avicel® PH105, Emcocel®, Vivacel®, Ming Tai® or Salka-Floc®), and the like can be given. Also, alginic acids or alginates and polyvinylpyrrolidone (e.g. Polyvidon® CL, Polyvidon® CL-M, Kollidon® CL, Polyplasdone® XL or Polyplasdone® XL-10), and the like can be used as disintegrant.

As examples of flavouring agents, perfume, lemon, lemon-lime, orange, menthol, peppermint oil, vanillin or powders of these absorbed with dextrin or cyclodextrin, and the like can be used.

As examples of lubricants or plasticizers, fatty acids or fatty acid derivatives such as magnesium stearate, sodium fumarate stearyl, calcium stearate, glyceryl monostearate, glycerylpalmitostearate, sodium laurylsulfate, stearic acid or zinc stearate; hydrogenated vegetable oils, such as hydrogenated castor oil; polyalkylene glycols, such as polyethylene glycol or polyethylene glycol glyceride (e.g. lauroyl polyoxylglyceride, such as Gelucire® 44/14); sodium benzoate; talc; colloidal silicon dioxide (Aerosil 200®) and the like can be given.

As examples of colorants, food dyes such as food yellow No. 5, food red No. 3, food blue No. 2, food lake dye, red iron oxide and the like can be given.

As examples of the stabilizer or solubilizer, antioxidants such as ascorbic acid and tocopherol, surfactants such as polysorbate 80 and the like can be given depending on the physiologically active component used.

As examples of filler, sucrose, glucose, lactose (e.g. spray-dried lactose, α-lactose, β-lactose, monohydrated lactose, Tablet-tose®, Pharmatose® or Fast-Floc®), mannitol, xylitol, dextrose, microcrystalline cellulose (e.g. Avicel®, such as Avicel® PH101, Avicel® PH102 or Avicel® Avicec PH105, Emcocel®, Vivacel®, Ming Tai® or Salka-Floc®), maltose, sorbitol, starches (including corn starch, potato starch and pregelatinized starch), sodium phosphate, calcium phosphate, calcium sulphate, calcium carbonate and the like can be given.

As an example of a foaming agent, sodium bicarbonate can be used.

As examples of sweeteners, sodium saccharin, dipotassium glycyrrhizin, aspartame, stevia, thaumatin and the like can be given.

In another particular embodiment, the composition of the invention further comprises a lubricant or plasticizer. In a preferred embodiment, the lubricant or plasticizer is selected from polyethylenglycol, preferably polyethylenglycol with an average weight between 7000 and 9000; polyethyleneglycol glyceride (e.g. lauroyl polyoxylglyceride, such as Gelucire® 44/14); or mixtures thereof.

According to another embodiment, the diluent or hinder is microcrystalline cellulose (e.g. Avicel®, such as Avicel® PH-101, Avicel® PH-102 or Avicel® PH-105, Emcocel®, Vivacel®, Ming Tai® or Salka-Floc®) or lauroyl polyoxylglyceride. Said pharmaceutical formulations comprising microcrystalline cellulose or lauroyl polyoxylglyceride may further comprise an excipient, preferably selected from water; sugars, such as hydrated or anhydrous dextrose, sucrose, galactose, maltose and lactose; starch or starch derivatives, including pregelatinized starch (Starch 1500 or National 1551), sodium starch glycollate, maize starch, potato starch, rice starch and wheat starch; ethyl cellulose; or synthetic polymers, such as polyvinylpyrrolidone (e.g. Polyvidon® CL, Polyvidon® CL-M, Kollidon® CL, Polyplasdone® XL or Polyplasdone® XL-10) and polyethylene glycol. Preferably, they may further comprise water, lactose monohydrate, pregelatined starch, polyethylene glycol with an average weight between 7000 and 9000, or mixtures thereof.

The formulation of the invention may further comprise a release controlling agent. Suitable controlling agents include cellulose derivatives such as ethyl cellulose, preferably in the form of aqueous dispersions (e.g. Surelease®), hydroxyethyl cellulose, hydroxypropyl cellulose, hydroxypropyl methyl-cellulose, polyvinylpyrrolidone, polyvinylpyrrolidone/vinyl acetate copolymer, and the like.

In a particular embodiment, the formulation of the invention is for oral, topical or parenteral administration; preferably it is an oral pharmaceutical formulation.

In an embodiment the formulation of the invention is in the form of a granule, a pellet or a bead. In a preferred embodiment, the formulation of the invention is a pellet.

In another embodiment, the formulation of the invention is comprised within a pharmaceutical dosage form such as a capsule, an ovule, a suppository, a wafer, a mini-tablet, a tablet, including a chewable tablet, a buccal tablet, a sublingual tablet, a quick-dissolve tablet, an effervescent tablet, a pill, a sachet, a sprinkle, a film, a dry syrup, a reconstitutable solid, a microsphere, a matrix, a gel, a dispersion, a solution, a suspension, a lozenge, a troche, an implant, a powder, a triturate, a platelet, or a strip.

In a particular embodiment, the formulation of the invention is in the form of pellets contained within a capsule. In another embodiment, it is in the form of pellets that are compressed into a tablet.

In a particular embodiment, the formulation of the invention is for immediate release, which is advantageous for example in the treatment of pain.

The formulations of the invention may be produced following methods known in the art (see "Remington, the Science and practice of pharmacy", $21^{st}$ Edition, 2005, Ed. Lippincott Williams & Wilkins). For example, a review of the different methods for obtaining pellets for pharmaceutical purposes can be found in the book Pharmaceutical Pelletization Technology, edited by Isaac Ghebre-Sellassie, Marcel Dekker, Inc., 1989.

According to a further aspect, the formulation of the invention may be prepared by a direct compression process, a granulation, extrusion/spheronization or layering process; preferably by an extrusion/spheronization or a melt granule process.

The production of pellet formulae by the extrusion/spheronization process involves generally the following steps:
1. Granulation: preparing a wet formulation mass.
2. Extrusion: shaping the wet formulation mass into cylinders.
3. Spheronization: breaking up the extrudate and rounding the resulting particles into spherical pellets.
The spheronization process can be divided into various stages according to the modifications of the shape of the extrudate. The following forms are produced in the process: cylinder/rope/dumb-bell/sphere with cavity/sphere.
4. Drying: desiccating the pellets.
5. Sieving: sifting the dried pellets.

The production of pellet formulae by the melt granulation process involves generally the following steps:
1. Granulation, by heating the formulation mixture.
2. Pelletization, by cooling the granules.
3. Sieving the dried pellets.

Active Pharmaceutical Ingredient

The active pharmaceutical ingredient of the composition of the invention is a compound of formula (I) as defined above.

In a particular embodiment, the active pharmaceutical ingredient is a compound of the formula (I) or (IB) as defined in WO 2006/021462, or a pharmaceutically acceptable salt, isomer, prodrug or solvate thereof. WO 2006/021462, which discloses these compounds, is incorporated herein in its entirety by reference.

Therefore, in a first embodiment the invention is directed to a pharmaceutical composition that comprises a compound of formula (IA):

(IA)

wherein
R$_1$ is selected from the group consisting of hydrogen, substituted or unsubstituted alkyl, substituted or unsubstituted cycloalkyl, substituted or unsubstituted alkenyl, substituted or unsubstituted arylalkyl, substituted or unsubstituted non-aromatic heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen;

R$_2$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen;

R$_3$ and R$_4$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen, or together they form a fused ring system;

R$_5$ and R$_9$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen;

or together form, with the nitrogen atom to which they are attached, a substituted or unsubstituted heterocyclyl group;

n is 1, 2, 3, 4, 5, 6, 7 or 8;
t is 1, 2 or 3;
R$_8$ and R$_9$ are each independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, and halogen;

or a pharmaceutically acceptable salt, isomer, prodrug or solvate thereof.

In a second embodiment the invention is directed to a pharmaceutical composition that comprises a compound of formula (IB):

(IB)

wherein
R$_1$ is selected from the group consisting of substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted aromatic heterocyclyl, substituted or unsubstituted non-aromatic heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —NR$_8$R$_9$, —NR$_8$C(O)R$_9$, —NO$_2$, —N=CR$_8$R$_9$, and halogen, R$_2$ is selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen;

R$_3$ and R$_4$ are independently selected from the group consisting of substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen, or together they form a fused ring system, R$_5$ and R$_6$ are independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted arylalkyl, substituted or unsubstituted heterocyclyl, substituted or unsubstituted heterocyclylalkyl, —COR$_8$, —C(O)OR$_8$, —C(O)NR$_8$R$_9$, —CH=NR$_8$, —CN, —OR$_8$, —OC(O)R$_8$, —S(O)$_t$—R$_8$, —NR$_8$R$_9$, —NR$_8$C(O)R$_9$, —NO$_2$, —N=CR$_8$R$_9$, and halogen; or together form, with the nitrogen atom to which they are attached, a substituted or unsubstituted heterocyclyl group;

n is 1, 2, 3, 4, 5, 6, 7 or 8;

t is 1, 2 or 3;

R$_8$ and R$_9$ are each independently selected from the group consisting of hydrogen, substituted or unsubstituted alkyl, substituted or unsubstituted cycloalkyl, substituted or unsubstituted alkenyl, substituted or unsubstituted aryl, substituted or unsubstituted heterocyclyl, substituted or unsubstituted alkoxy, substituted or unsubstituted aryloxy, and halogen;

or a pharmaceutically acceptable salt, isomer, prodrug or solvate thereof.

In the present description the following terms have the meaning indicated:

"Alkyl" refers to a straight or branched hydrocarbon chain radical consisting of carbon and hydrogen atoms, containing no unsaturation, having one to eight carbon atoms, and which is attached to the rest of the molecule by a single bond, e. g., methyl, ethyl, n-propyl, i-propyl, n-butyl, t-butyl, n-pentyl, etc. Alkyl radicals may be optionally substituted by one or more substituents such as a aryl, halo, hydroxy, alkoxy, carboxy, cyano, carbonyl, acyl, alkoxycarbonyl, amino, nitro, mercapto, alkylthio, etc. If substituted by aryl we have an "Aralkyl" radical, such as benzyl and phenethyl.

"Alkenyl" refers to an alkyl radical having at least 2C atoms and having one or more unsaturated bonds.

"Cycloalkyl" refers to a stable 3- to 10-membered monocyclic or bicyclic radical which is saturated or partially saturated, and which consist solely of carbon and hydrogen atoms, such as cyclohexyl or adamantyl. Unless otherwise stated specifically in the specification, the term "cycloalkyl" is meant to include cycloalkyl radicals which are optionally substituted by one or more substituents such as alkyl, halo, hydroxy, amino, cyano, nitro, alkoxy, carboxy, alkoxycarbonyl, etc.

"Aryl" refers to single and multiple ring radicals, including multiple ring radicals that contain separate and/or fused aryl groups. Typical aryl groups contain from 1 to 3 separated or fused rings and from 6 to about 18 carbon ring atoms, such as phenyl, naphthyl, indenyl, fenanthryl or anthracyl radical. The aryl radical may be optionally substituted by one or more substituents such as hydroxy, mercapto, halo, alkyl, phenyl, alkoxy, haloalkyl, nitro, cyano, diatkylamino, aminoalkyl, acyl, alkoxycarbonyl, etc.

"Heterocyclyl" refers to a stable 3- to 15 membered ring radical which consists of carbon atoms and from one to five heteroatoms selected from the group consisting of nitrogen, oxygen, and sulfur, preferably a 4- to 8-membered ring with one or more heteroatoms, more preferably a 5- or 6-membered ring with one or more heteroatoms. It may be aromatic or not aromatic. For the purposes of this invention, the heterocycle may be a monocyclic, bicyclic or tricyclic ring system, which may include fused ring systems; and the nitrogen, carbon or sulfur atoms in the heterocyclyl radical may be optionally oxidised; the nitrogen atom may be optionally quaternized; and the heterocyclyl radical may be partially or fully saturated or aromatic. Examples of such heterocycles include, but are not limited to, azepines, benzimidazole, benzothiazole, furan, isothiazole, imidazole, indole, piperidine, piperazine, purine, quinoline, thiadiazole, tetrahydrofuran, coumarine, morpholine; pyrrole, pyrazole, oxazole, isoxazole, triazole, imidazole, etc.

"Alkoxy" refers to a radical of the formula —ORa where Ra is an alkyl radical as defined above, e. g., methoxy, ethoxy, propoxy, etc.

"Amino" refers to a radical of the formula —NH$_2$, —NHRa or —NRaRb, optionally quaternized.

"Halo" or "hal" refers to bromo, chloro, iodo or fluoro.

References herein to substituted groups in the compounds of the present invention refer to the specified moiety that may be substituted at one or more available positions by one or more suitable groups, e. g., halogen such as fluoro, chloro, bromo and iodo; cyano; hydroxyl; nitro; azido; alkanoyl such as a C1-6 alkanoyl group such as acyl and the like; carboxamido; alkyl groups including those groups having 1 to about 12 carbon atoms or from 1 to about 6 carbon atoms and more preferably 1-3 carbon atoms; alkenyl and alkynyl groups including groups having one or more unsaturated linkages and from 2 to about 12 carbon or from 2 to about 6 carbon atoms; alkoxy groups having one or more oxygen linkages and from 1 to about 12 carbon atoms or 1 to about 6 carbon atoms; aryloxy such as phenoxy; alkylthio groups including those moieties having one or more thioether linkages and from 1 to about 12 carbon atoms or from 1 to about 6 carbon atoms; alkylsulfinyl groups including those moieties having one or more sulfinyl linkages and from 1 to about 12 carbon atoms or from 1 to about 6 carbon atoms; alkylsulfonyl groups including those moieties having one or more sulfonyl linkages and from 1 to about 12 carbon atoms or from 1 to about 6 carbon atoms; aminoalkyl groups such as groups having one or more N atoms and from 1 to about 12 carbon atoms or from 1 to about 6 carbon atoms; carbocylic aryl having 6 or more carbons, particularly phenyl or naphthyl and aralkyl such as benzyl. Unless otherwise indicated, an optionally substituted group may have a substituent at each substitutable position of the group, and each substitution is independent of the other.

Unless otherwise stated, the compounds used as active ingredient in the composition of the invention are also meant to include compounds which differ only in the presence of one or more isotopically enriched atoms. For example, compounds having the present structures except for the replacement of a hydrogen by a deuterium or tritium, or the replacement of a carbon by a or $^{13}$C- or $^{14}$C-enriched carbon or $^{15}$N-enriched nitrogen are within the scope of this invention.

The term "salt" must be understood as any form of an active compound used in accordance with this invention in which said compound is in ionic form or is charged and coupled to a counter-ion (a cation or anion) or is in solution. This definition also includes quaternary ammonium salts and complexes of the active molecule with other molecules and ions, particularly, complexes formed via ionic interactions. The definition includes in particular physiologically acceptable salts; this term must be understood as equivalent to "pharmacologically acceptable salts".

The term "pharmaceutically acceptable salts" in the context of this invention means any salt that is tolerated physiologically (normally meaning that it is not toxic, particularly, as a result of the counter-ion) when used in an appropriate manner for a treatment, applied or used, particularly, in humans and/or mammals.

For instance, pharmaceutically acceptable salts of compounds provided herein are synthesized from the parent compound which contains a basic or acidic moiety by conventional chemical methods. Generally, such salts are, for example, prepared by reacting the free acid or base forms of these compounds with a stoichiometric amount of the appropriate base or acid in water or in an organic solvent or in a mixture of the two. Generally, nonaqueous media like ether, ethyl acetate, ethanol, isopropanol or acetonitrile are preferred. Examples of the acid addition salts include mineral acid addition salts such as, for example, hydrochloride, hydrobromide, hydroiodide, sulphate, nitrate, phosphate, and organic acid addition salts such as, for example, acetate, maleate, fumarate, citrate, oxalate, succinate, tartrate, malate, mandelate, methanesulphonate and p-toluenesulphonate. Examples of the alkali addition salts include inorganic salts such as, for example, sodium, potassium, calcium, ammonium, magnesium, aluminium and lithium salts, and organic alkali salts such as, for example, ethylenediamine, ethanolamine, N,N-dialkylenethanolamine, triethanolamine, glutamine and basic aminoacids salts.

The term "solvate" in accordance with this invention should be understood as meaning any form of the active compound in accordance with the invention in which said compound is bonded by a non-covalent bond to another molecule (normally a polar solvent), including especially hydrates and alcoholates, like for example, methanolate. A preferred solvate is the hydrate.

The compounds of the invention may be in crystalline form either as free compounds or as solvates and it is intended that both forms are within the scope of the present invention. Methods of solvation are generally known within the art. Suitable solvates are pharmaceutically acceptable solvates. In a particular embodiment the solvate is a hydrate.

Any compound that is a prodrug of a compound of formula (I), (IA) or (IB) is also within the scope of the invention. The term "prodrug" is used in its broadest sense and encompasses those derivatives that are converted in vivo to the compounds of the invention. Examples of prodrugs include, but are not limited to, derivatives and metabolites of the compounds of formula I that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Preferably, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger "Medicinal Chemistry and Drug Discovery 6th ed. (Donald J. Abraham ed., 2001, Wiley), "Design and Applications of Prodrugs" (H. Bundgaard ed., 1985, Harwood Academic Publishers) and Krogsgaard-Larsen et al. "Textbook of Drug design and Discovery" Taylor & Francis (April 2002).

The term "pharmaceutically acceptable salts, solvates, prodrugs" refers to any pharmaceutically acceptable salt, ester, solvate, or any other compound which, upon administration to the recipient is capable of providing (directly or indirectly) a compound as described herein. However, it will be appreciated that non-pharmaceutically acceptable salts also fall within the scope of the invention since those may be useful in the preparation of pharmaceutically acceptable salts. The preparation of salts, prodrugs and derivatives can be carried out by methods known in the art.

The compounds of the present invention represented by the above described formula (I), (IA) or (IB) may include enantiomers depending on the presence of chiral centres or isomers depending on the presence of multiple bonds (e.g. Z, E). The single isomers, enantiomers or diastereoisomers and mixtures thereof fall within the scope of the present invention.

The compounds of formula (I), (IA) or (IB) or their salts or solvates are preferably in pharmaceutically acceptable or substantially pure form. By pharmaceutically acceptable form is meant, inter alia, having a pharmaceutically acceptable level of purity excluding normal pharmaceutical additives such as diluents and carriers, and including no material considered toxic at normal dosage levels. Purity levels for the drug substance are preferably above 50%, more preferably above 70%, most preferably above 90%. In a preferred embodiment it is above 95% of the compound of formula (I), (IA) or (IB), or of its salts, solvates or prodrugs.

In a particular embodiment, $R_1$ is selected from H, —$COR_8$, or substituted or unsubstituted alkyl, preferably it is selected from H, methyl or acetyl.

In another embodiment $R_2$ is H or alkyl, preferably H or methyl.

In another embodiment $R_3$ and $R_4$ are independently selected from halogen or alkyl, preferably from halogen or haloalkyl; or they form, together with the phenyl group to which they are attached, a fused ring system, preferably a naphthyl group.

It is preferred that the aryl substituents $R_3$ and $R_4$ are situated in the meta and/or para positions of the phenyl group.

Further, in a preferred embodiment n is preferably 2, 3, 4, 5, or 6 most preferably n is 2, 3 or 4. A most preferred value for n is 2.

In another preferred embodiment $R_5$ and $R_6$ are an alkyl group, preferably ethyl; or together with the nitrogen atom to which they are attached, form a substituted or unsubstituted 5- or 6-membered heterocyclyl group, preferably a substituted or unsubstituted pyrrolidine, piperidine, piperazine-4-yl or morpholine-4-yl group.

In a particular embodiment, the active pharmaceutical ingredient is selected from:
1-(3,4-Dichlorophenyl)-5-methyl-3-[2-(pyrrolidin-1-yl) ethoxy]-1H-pyrazole,
1-{2-[1-(3,4-Dichlorophenyl)-5-methyl-1H-pyrazol-3-yloxy]ethyl}-4-methylpiperazine,
1-(4-(2-(1-(3,4-dichlorophenyl)-1H-pyrazol-3-yloxy)ethyl) piperidin-1-yl)ethanone,
2-[1-(2,4-dichlorophenyl)-1H-pyrazol-3-yloxy]N,N-diethylethanamine,
2-[1-(3,4-Dichlorophenyl)-4,5-dimethyl-1H-pyrazol-3-yloxy]-N,N-diethylethanamine,
4-[1-(3,4-dichlorophenyl)-1H-pyrazol-3-yloxy]-N,N-diethylbutan-1-amine,
1-{2-[5-Methyl-1-(naphthalen-2-yl)-1H-pyrazol-3-yloxy] ethyl}piperidine,
1-(4-(2-(1-(naphthalen-2-yl)-1H-pyrazol-3-yloxy)butyl)piperazin-1-yl)ethanone, and
4-{2-[5-Methyl-1-(naphthalen-2-yl)-1H-pyrazol-3-yloxy] ethyl}morpholine,
their salts, prodrugs or solvates. Preferably, in their free form or as a hydrochlorate or oxalate salt.

In a preferred embodiment the active pharmaceutical ingredient is 4-{2-[5-Methyl-1-(naphthalen-2-yl)-1H-pyrazol-3-yloxy]ethyl}morpholine hydrochloride, hereinafter ed to as API-001.

In additional preferred embodiments, the preferences described above for the different substituents are combined. The present invention is also directed to such combinations of preferred substitutions of general formula (I), (IA) and (IB) above.

Another aspect of the present invention refers to the pharmaceutical composition of the invention for use as a medicament.

Another aspect relates to the pharmaceutical composition of the invention for use in the treatment or prophylaxis of a sigma receptor mediated disease or condition. In a particular embodiment the disease is selected from the group consisting of diarrhea; lipoprotein disorders; migraine; obesity; arthritis; hypertension; arrhythmia; ulcer; learning, memory and attention deficits; cognition disorders; neurodegenerative diseases; demyelinating diseases; addiction to drugs and chemical substances including cocaine, amphetamine, ethanol and nicotine; tardive diskinesia; ischemic stroke; epilepsy; stroke; stress; cancer; psychotic conditions, in particular depression, anxiety or schizophrenia; inflammation; and autoimmune diseases. In another particular embodiment the disease is pain, preferably neuropathic pain, inflammatory pain or other pain conditions involving allodynia and/or hyperalgesia.

Another aspect of this invention relates to a method of treating or preventing a sigma receptor mediated disease which method comprises administering to a patient in need of such a treatment a therapeutically effective amount of the pharmaceutical composition of the invention. Among the sigma mediated diseases that can be treated are diarrhea; lipoprotein disorders; migraine; obesity; arthritis; hypertension; arrhythmia; ulcer; cognition disorders; addiction to chemical substances such as cocaine dependency; tardive diskinesia; ischemic stroke; epilepsy; stroke; depression; stress; pain, especially neuropathic pain or allodynia; psychotic condition; or cancer. The compounds of the invention can also be employed as pharmacological tool or as anxiolytic or immunosuppressant.

The following examples are given only as further illustration of the invention, they should not be taken as a definition of the limits of the invention.

EXAMPLES

The following abbreviations have been used:
API-001—4-{2-[5-Methyl-1-(naphthalen-2-yl)-1H-pyrazol-3-yloxy]ethyl}morpholine hydrochloride
PEG 8000—polyethylene glycol having a molecular weight of 8000
Starch 1500—partially pregelatinized maize starch
Avicel® PH-101—high purity microcrystalline cellulose of 50 μm particle size
 (FMC Corp, Delaware, US)
Avicel® PH-102—high purity microcrystalline cellulose of 100 μm particle size
 (FMC Corp, Delaware, US)
Surelease®—aqueous ethylcellulose dispersion (Colorcon, BPSI Holdings
 LLC, Pennsylvania, US)
Gelucire® 44/14/PEG—polyethylene glycol glycerides composed of mono-, di- and
 triglycerides and mono- and diesters of polyethylene glycol 1. Pellet General Characteristics Four pellet formulations containing 4-{2-[5-Methyl-1-(naphthalen-2-yl)-1H-pyrazol-3-yloxy]ethyl}morpholine hydrochloride and different excipients (experimental blocks) were prepared. For each experimental block four specific formulations containing variable proportions of the same excipients (examples) were made. Experimental blocks nos. 1, 2 and 3 pellets were developed by the extrusion/spheronization process. Experimental block no. 4 pellets were developed by the melt granulation process.

The following tables describe the percentage formulae compositions of each example:

TABLE 1

Experimental Block No. 1. Extrusion/spheronization process.

|  | Pattern −/+ Example 001 | Pattern +/− Example 002 | Pattern +/+ Example 003 | Pattern −/− Example 004 |
|---|---|---|---|---|
| API-001 | 87.4% | 87.4% | 85.4% | 89.4% |
| PEG 8000 | 2.9% | 4.9% | 4.9% | 2.9% |
| Avicel ® PH-102 | 9.7% | 7.7% | 7.7% | 9.7% |
| Purified water | — | — | — | — |
| Ratio PEG/MCC | 3.345 | 1.571 | 1.980 | 2.655 |

TABLE 2

Experimental Block No. 2. Extrusion/spheronization process

|  | Pattern −/+ Example 005 | Pattern +/− Example 006 | Pattern +/+ Example 007 | Pattern −/− Example 008 |
|---|---|---|---|---|
| API-001 | 87.4% | 87.4% | 85.4% | 89.4% |
| Starch 1500 | 3% | 4% | 4% | 3% |
| Avicel ® PH-101 | 3% | 4% | 4% | 3% |
| Lactose monohydrate | 6.6% | 4.6% | 6.6% | 4.6% |
| Water | — | — | — | — |
| Ratio Starch/MCC | 1.0 | 1.0 | 1.0 | 1.0 |

TABLE 3

Experimental Block No. 3. Extrusion/spheronization process

|  | Pattern −/+ Example 009 | Pattern +/− Example 010 | Pattern +/+ Example 011 | Pattern −/− Example 012 |
|---|---|---|---|---|
| API-001 | 87.4% | 87.4% | 85.4% | 89.4% |
| PEG 8000 | 2.9% | 4.9% | 4.9% | 2.9% |
| Avicel ® PH-102 | 9.7% | 7.7% | 9.7% | 7.7% |
| Surelease* | — | — | — | — |

The pellet core was modified by adding Surelease® ethylcellulose aqueous dispersion 25% dry to enable core release control.

TABLE 4

Experimental Block No. 4. Melt granulation process.

|  | Pattern −/+ Example 013 | Pattern +/− Example 014 (Comparative) | Pattern +/+ Example 015 (Comparative) | Pattern −/− Example 016 |
|---|---|---|---|---|
| API-001 | 80.0% | 78.3% | 76.0% | 90.0% |
| Lactose monohydrate | 0.0% | 6.6% | 7.3% | 0.0% |
| Gelucire ® 44/14/PEG | 20.0% | 15.1% | 16.7% | 10.0% |

2. Description of General Processes
 a) Extrusion/Spheronization Process
 The experimental blocks nos. 1, 2 and 3 pellets were prepared according to the following protocol:
 1) Blend/Granulation
 A 900 ml volume vessel was used. A batch mixture size of 150 g was prepared. The batch mixture was blended and granulated utilizing a high shear mixer under the following parameters:

| Parameters | Blend | Granulation |
|---|---|---|
| Impeller speed | 800 rpm | 1100 rpm |
| Chopper speed | — | 3000 rpm |
| Blend/massing time | 2 min | Aprox. 4-6 min |
| Liquid granulation (water + PEG 8000) | — (6 ml/min) | Aprox. 30-34 min |

2) Extrusion

The granules obtained from the preceding step were shaped into long rods or extrudates. The extruder was set at a 50-70 g load and a 50 rpm screw speed. A 1.0 mm die was used.

3) Spheronization

The extrudate from the preceding step was shaped into spherical pellets with a spheronizer. The extruder was set at a 50-70 g load and a 2000 rpm plate speed for 4 minutes. A 3.25 mm plate was utilized. A 2.0 mm plate could be utilized alternatively to increase productivity. The addition of MCC as lubricant during the spheronization phase was optional.

4) Drying

The pellets obtained from spheronization process were dried in a fluid bed dryer. The dryer was set at a temperature of 55° C. for 15 minutes.

5) Sieving

After drying, the pellets were sifted through a 0.5-1.4 mm sieve.

b) Melt Granulation Process

Experimental block no. 4 was prepared according to the following protocol:

1) Blend/Granulation

A 900 ml volume vessel was used. Batch mixture sizes of 144 to 159.0 g were prepared. The batch mixtures were granulated utilizing a high shear mixer under the following parameters:

| Parameters | Blend | Granulation |
|---|---|---|
| Impeller speed | 1200 rpm | 800 rpm |
| Chopper speed | 300 rpm | 1400 rpm |
| Blend/Massing time | 10-15 min | 10-15 min |

The mixtures were then heated at 55° C. in a bowl jacket for approximately 10 to 15 minutes. The binder melted when the mixtures reached a temperature of 45-55° C.

2) Pelletization

The granules obtained from the preceding step were cooled at 5° C. in a bowl jacket for approximately 10 to 15 minutes. The pellets formed when the granules reached a temperature of 25° C.

3) Sieving

After cooling, the pellets were sifted through a 0.5-1.4 mm sieve.

A. Preparation of Experimental Block No. 1 Pellets

Formulation mixtures were prepared by dissolving PEG 8000 in purified water 16.6% (25 ml) to obtain a binding solution. This binding solution was added to a mixture of API-001 and Avicel® PH-102 microcrystalline cellulose in the granulator, and the mixture kneaded until granulation end point. The granules were extruded, spheronized and dried according to the extrusion/spheronization general protocol. The resulting pellets were sifted with 0.5-1.4 mm sieve to obtain formulation mixtures with the following content specifications:

| Experimental Block No. 1. Extrusion/spheronization process | | | | |
|---|---|---|---|---|
| | Pattern −/+ Example 001 | Pattern +/− Example 002 | Pattern +/+ Example 003 | Pattern −/− Example 004 |
| API-001 | 131.1 g | 131.1 g | 128.1 g | 134.1 g |
| PEG 8000 | 4.35 g | 7.35 g | 7.35 g | 4.35 g |
| Avicel® PH-102 | 14.55 g | 11.55 g | 14.55 g | 11.55 g |
| Water | (25 g) | (25 g) | (25 g) | (25 g) |
| Total weight | 150 g | 150 g | 150 g | 150 g |
| Binding solution | 29.35 g | 32.35 g | 32.35 g | 29.35 g |
| % water | 16.60% | 16.60% | 16.60% | 16.60% |

Binding solution was adjusted after the first granulation trial.

B. Preparation of Experimental Block No. 2 Pellets

Purified water 10.6% (16 ml) was used as a binding solution. API-001, Starch 1500, Avicel® PH-101 microcrystalline cellulose and lactose monohydrate were blended in the granulator and the mixture kneaded until granulation end point. The granules were extruded, spheronized and dried according to the extrusion/spheronization general protocol. The resulting pellets were sifted with 0.5-1.4 mm sieve to obtain formulation mixtures with the following content specifications:

| Experimental Block No. 2. Extrusion/spheronization process. | | | | |
|---|---|---|---|---|
| | Pattern −/+ Example 005 | Pattern +/− Example 006 | Pattern +/+ Example 007 | Pattern −/− Examle 008 |
| API-001 | 131.1 g | 131.1 g | 128.1 g | 134.1 g |
| Starch 1500 | 4.5 g | 6.0 g | 6.0 g | 4.5 g |
| Avicel® PH-101 | 4.5 g | 6.0 g | 6.0 g | 4.5 g |
| Lactose monohydrate | 9.9 g | 6.9 g | 9.9 g | 6.9 g |
| Water | (16 g) | (16 g) | (16 g) | (16 g) |
| Total weight | 150 g | 150 g | 150 g | 150 g |
| Binding solution | 16 g | 16 g | 16 g | 16 g |
| % water | 10.66% | 10.66% | 10.66% | 10.66% |

Binding solution was adjusted after the first granulation trial.

C. Preparation of Experimental Block No. 3 Pellets

Surelease® aqueous dispersion with a 25% dry ethyl cellulose content (34 ml, 22.64%) was used as a binding solution. API-001, PEG 8000 and Avicel® PH-102 microcrystalline cellulose were blend in the granulator, and the mixture kneaded until granulation end point. The granules were extruded, spheronized and dried according to the extrusion/spheronization general protocol. The resulting pellets were sifted with 0.5-1.4 mm sieve to obtain formulation mixtures with the following content specifications:

| Experimental Block No. 3. Extrusion/spheronization process. | | | | |
|---|---|---|---|---|
| | Pattern −/+ Example 005 | Pattern +/− Example 006 | Pattern +/+ Example 007 | Pattern −/− Example 008 |
| API-001 | 131.1 g | 131.1 g | 128.1 g | 134.1 g |
| PEG 8000 | 4.35 g | 7.35 g | 7.35 g | 4.35 g |
| Avicel® PH-102 | 14.55 g | 11.55 g | 14.55 g | 11.55 g |
| Surelease® | (9 g) | (8.5 g) | (8.5 g) | (8.5 g) |
| Total weight | 150 g | 150 g | 150 g | 150 g |
| % Surelease® | 22.64% | 21.38% | 21.38% | 21.38% |

Binding solution was adjusted after the first granulation trial.

D. Preparation of Experimental Block No. 4 Pellets

API-001, lactose monohydrate and Gelucire® 44/14/PEG were combined. The resulting mixture was heated in a bowl jacket at 55° C. for aprox. 10-15 min. The binder melted when the mixture temperature was about 45-50° C. The resulting granules were cooled down in a bowl jacket at 5° C. for aprox. 10-15 min. The pellets were formed when the granules reached 25° C. The pellets were sifted with a 0.5-1.4 mm sieve to obtain formulation mixtures with the following content specifications:

Experimental Block No. 4. Melt granulation process.

|  | Pattern −/+ Example 013 | Pattern +/− Example 014 (Comparative) | Pattern +/+ Example 015 (Comparative) | Pattern −/− Example 016 |
|---|---|---|---|---|
| API-001 | 120 g | 124.5 g | 109.5 g | 135 g |
| Lactose monohydrate | 0 g | 10.5 g | 10.5 g | 0 g |
| Gelucire ® 44/14/PEG | 30 g | 24 g | 24 g | 15 g |
| Total weight | 150.0 g | 159.0 g | 144.0 g | 150.0 g |
| Binder content | 20% | 15.1% | 16.7% | 10.0% |

E. Assays Performed on API-001 Immediate Release Pellets

Figure 1:
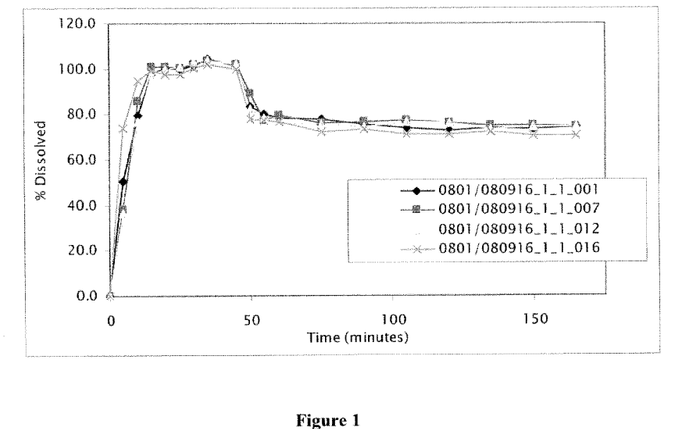
FIG. 1 shows the dissolution profiles of immediate release pellets for representative formulations of experimental block nos. 1, 2, 3 and 4, under the following conditions; acidic medium of HCl 0.1N pH 1.2 and buffer solution at pH 5.5 and 6.8, paddle speed 50 rpm and volume 900 ml. Sink conditions were maintained in acidic medium HCl 0.1N pH 1.2 and buffer solution pH 5.5, non-sink conditions was conducted when the medium was change to pH 6.8. The last three numbers of the legend names refer to the corresponding example numbers.

Representative members of each experimental block were assayed according to various parameters. In some cases all the members of each experimental block were tested. In the first test, the pellets' appearance, % impurities, dissolution profiles at pH 5.5 and pH 6.8 at 15 minutes were assayed. See Table 5. The second analysis assessed their particle size, % roundness, % KF and yields after a 500-1400 μm sieving process. See Table 6. The third assay examined the pellets' dissolution profiles under varying pH conditions. See FIG. 1.

TABLE 5

Values for appearance assay, % total impurities and % dissolution at pH 5.5 and pH 6.8.

| Example | Assay % | Total Impurities % | Dissolution profile buffer solution at pH 5.5 at 15 min. | Dissolution profile buffer solution at pH 6.8 at 15 min. |
|---|---|---|---|---|
| 001 | 99.04 | <0.07 | 97.00 | 85.5 |
| 002 | — | — | — | — |
| 003 | 98.49 | <0.07 | 95.56 | 87.9 |
| 004 | 97.75 | <0.08 | 96.13 | 89.2 |
| 005 | 97.08 | <0.06 | 94.96 | 89.4 |
| 006 | 98.65 | <0.07 | 96.17 | 87.9 |
| 007 | 98.20 | <0.06 | 97.60 | 81.7 |
| 008 | 96.75 | <0.04 | 95.56 | 89.5 |
| 009 | 96.05 | <0.07 | 88.44 | 67.3 |
| 010 | 96.00 | <0.08 | 82.73 | 67.8 |
| 011 | 96.30 | <0.07 | 81.31 | 67.9 |
| 012 | 97.00 | <0.10 | 77.91 | 68.9 |
| 013 | — | — | — | — |
| 014 | — | — | — | — |
| 015 | 98.40 | <0.08 | 105.8 | 86.0 |
| 016 | 95.60 | <0.11 | 93.29 | 80.7 |

TABLE 6

Values for media particle size, % roundness, % Kf and yields after sieving process 500-1400 μm.

| Example | Particle size media (μm) | % Kf | IH |
|---|---|---|---|
| 001 | 981.1 | 0.73 | 1.01 |
| 002 | — | — | — |
| 003 | 999.4 | 0.65 | 1.04 |
| 004 | 914.0 | 0.54 | 1.03 |
| 005 | 928.9 | 2.1 | 10.4 |
| 006 | 925.9 | 0.87 | 1.04 |
| 007 | 937.6 | 1.37 | 1.00 |
| 008 | 922.8 | 1.39 | 1.04 |
| 009 | 1010.1 | 0.45 | 1.03 |
| 010 | 950.9 | 0.43 | 1.01 |
| 011 | 995.3 | 0.53 | 1.05 |
| 012 | 981.8 | 0.44 | 1.05 |
| 013 | — | — | — |
| 014 | — | — | — |
| 015 | 1030.6 | 0.52 | 1.03 |
| 016 | 964.0 | 0.15 | 1.01 |

F. API-001 Release Optimization by Varying Formulation Parameters

A full factorial design (2×2×2×2) study was performed over formulation mixtures with percentage compositions of examples nos. 001, 002 and 004. The purpose of the study was to determine the effect of changes in certain selected variables over the pellets' rates of release. The assayed variables were:
a) ratio of excipients,
b) % binding solution,
c) spheronization speed, and
d) spheronization time.

The ranges of the study variables were defined as follows:

| | | Factorial code | | |
|---|---|---|---|---|
| | | 1 | 0 | −1 |
| Designation | Variable | High value | Middle value | Low value |
| X1 | Ratio of excipients MCC/PEG 8000 | 3.345 | 2.655 | 1.571 |
| X2 | Binding solution | 21.3% (32 g) | 20.0% (30 g) | 18.7% (28 g) |
| X3 | Spheronization speed | 1800 rpm | 1500 rpm | 800 rpm |
| X4 | Spheronization time | 6 min | 4 min | 2 min |

For comparison and analysis purposes the formulation mixtures prepared according to examples nos. 001, 002 and 004 were assigned factorial codes 1, −1 and 0, respectively.

The examples nos. 001, 002 and 004 formulation mixtures were processed according to the extrusion/spheronization protocol above. The following protocol modifications were performed:

During the blend granulation step, batch mixtures of 150 g were prepared. The batch mixtures were blended and granulated utilizing a high shear mixer under the following parameters:

| Parameters | Blend | Granulation |
|---|---|---|
| Impeller speed | 500 rpm | 1000 rpm |
| Chopper speed | — | 3000 rpm |
| Blend/massing time | 1 min | Aprox. 4-5 min |
| Nozzle | — | 04 mm |
| Spray rate | — | 6 ml/min |

Afterwards, the granules obtained from the preceding step were shaped into long rods or extrudates with a laboratory extruder. The extruder was set at a 150 g load and a 50 rpm screw speed. A 1.0 mm die was utilized. The resulting extrudates were shaped into spherical pellets with a laboratory spheronizer. For this step, the extruder was set at a 150 g load, variable plate speed and variable spheronization time. A 2.0 mm plate was utilized. Then, the pellets obtained from spheronization process were dried in a 5-liter fluid bed dryer. The dryer was set at a temperature of 55° C. for 15 minutes.

Figure 2:
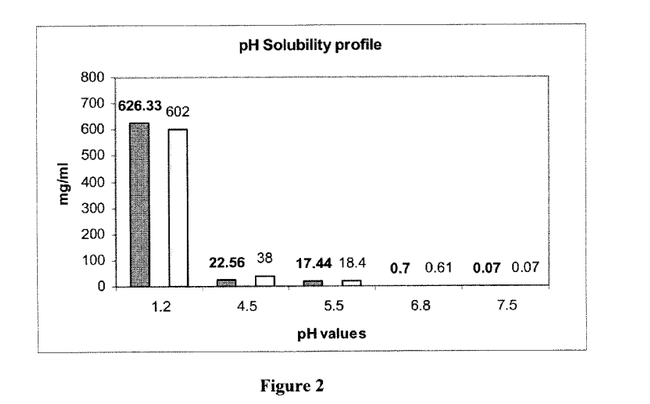
FIG. 2 shows the pH solubility profile of API-001.

The API-001 release profile of the various pellet formulations prepared for the full factorial design (2×2×2×2) study were assayed at 10 and 15 minutes after dissolution. Table 7 illustrates the parameters applied and results obtained at 10 minutes from dissolution:

As may be appreciated from the pH solubility profile shown in FIG. 2, solubility of API-001 is decreasing when is increasing the pH of the medium.

It is known that the use of microcrystalline cellulose (MCC) in pellets manufactured by extrusion can modify the release profile, delaying the release of the drug, especially for poorly soluble compounds (Duckic et al, "Production of pellets via extrusion-spheronization without the incorporation of microcrystalline cellulose: A critical review" European Journal of Pharmaceutics and Biopharmaceutics, vol. 71. no. 1, 2009; Kranz et al. "Drug release from MCC- and carrageenan-based pellets: Experimental and theory" European Journal of Pharmaceutics and Biopharmaceutics, vol. 73, no. 2, 2009).

However, surprisingly in vitro drug release studies performed at different pH (acid HCl 0.1N pH 1.2, buffer solution pH 5.5 and buffer solution pH 6.8) show a fast release rate; independently of the solubility of API-001, more that 80% of drug is dissolved at first 15 minutes. The presence of MCC in the pellet composition does not prolong drug release rate, even when it is used at a medium buffer solution pH 6.8, equivalent to in vivo intestinal pH, where solubility of API-001 is extremely low 0.6 mg/ml (poorly soluble compound). Therefore, it is expected that the extrusion-spheronization pellets of the invention to be absorbed over all the intestinal tract.

Figure 3:
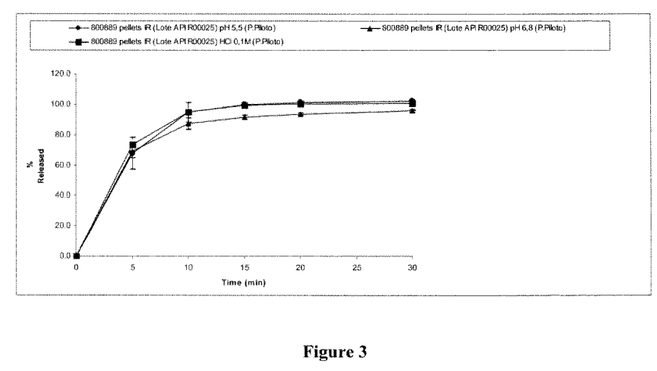
FIG. 3 represents the influence of drug solubility in the in vitro release profile of extrusion-spheronization pellets of API-001 (Sink conditions were maintained during all the study).

FIG. 3 represents the influence of drug solubility in the in vitro release profile of extrusion-spheronization pellets of API-001 (Sink conditions were maintained during all the study). In concrete, the tested formulation contained: 86.6% API-001, 2.9% PEG8000 as a binder and MCC 10.5% as a filler or aid for extrusion process.

4. Long Term Stability

The formulation developed made up of extrusion spheronization pellets with a high drug loading of 86.6% surprisingly maintains a fast release profile at long term stability studies

TABLE 7

Values for ratio of excipients, % granulation liquid, spheronization speed, spheronization time and % dissolution at pH 5.5.

| A | Ex | Pattern | | | | | X1 | X2 | X3 | X4 | | 10 min release |
|---|---|---|---|---|---|---|---|---|---|---|---|---|
| 1 | 001 | +++− | 1 | 1 | 1 | −1 | 3.345 | -21.3% | -1800 rpm | -2 min | | 87.4% |
| 2 | 001 | ++−− | 1 | 1 | −1 | −1 | 3.345 | -21.3% | -800 rpm | -2 min | | 87.4% |
| 3 | 001 | ++++ | 1 | 1 | 1 | 1 | 3.345 | -21.3% | -1800 rpm | -6 min | | 87.4% |
| 4 | 002 | −−−− | −1 | −1 | −1 | −1 | 1.571 | -18.7% | -800 rpm | -2 min | | 87.4% |
| 5 | 004 | 0000 | 0 | 0 | 0 | 0 | 2.655 | -20% | -1500 rpm | -4 min | | 89.4% |
| 6 | 002 | −+−+ | −1 | 1 | −1 | 1 | 1.571 | -21.3% | -800 rpm | -6 min | | 87.4% |
| 7 | 001 | +−+− | 1 | −1 | 1 | −1 | 3.345 | -18.7% | -1800 rpm | -2 min | | 87.4% |
| 8 | 001 | +−−+ | 1 | −1 | −1 | 1 | 3.345 | -18.7% | -800 rpm | -6 min | | 87.4% |
| 9 | 002 | −+−− | −1 | 1 | −1 | −1 | 1.571 | -21.3% | -800 rpm | -2 min | | 87.4% |
| 10 | 002 | −−−+ | −1 | −1 | −1 | 1 | 1.571 | -18.7% | -800 rpm | -6 min | | 87.4% |
| 11 | 002 | −++− | −1 | 1 | 1 | −1 | 1.571 | -21.3% | -1800 rpm | -2 min | | 87.4% |
| 12 | 002 | −−++ | −1 | −1 | 1 | 1 | 1.571 | -18.7% | -1800 rpm | -6 min | | 87.4% |
| 13 | 004 | 0000 | 0 | 0 | 0 | 0 | 2.655 | -20% | -1500 rpm | -4 min | | 89.4% |
| 14 | 004 | 0000 | 0 | 0 | 0 | 0 | 2.655 | -20% | -1500 rpm | -4 min | | 89.4% |
| 15 | 002 | −−+− | −1 | −1 | 1 | −1 | 1.571 | -18.7% | -1800 rpm | -2 min | | 87.4% |
| 16 | 001 | +−++ | 1 | −1 | 1 | 1 | 3.345 | -18.7% | -1800 rpm | -6 min | | 87.4% |
| 17 | 004 | 0000 | 0 | 0 | 0 | 0 | 2.655 | -20% | -1500 rpm | -4 min | | 89.4% |
| 18 | 001 | ++−+ | 1 | 1 | −1 | 1 | 3.345 | -21.3% | -800 rpm | -6 min | | 87.4% |
| 19 | 001 | +−−− | 1 | −1 | −1 | −1 | 3.345 | -18.7% | -800 rpm | -2 min | | 87.4% |
| 20 | 002 | −+++ | −1 | 1 | 1 | 1 | 1.571 | -21.3% | -1800 rpm | -6 min | | 87.4% |

Over more than 85% of API-001 was released after 15 minutes in all cases.

3. In Vitro Release Profile

API-001 has a pKa 6.8, being a weakly basic drug and having a solubility strongly influenced by pH of the medium.

under ambient at 25° C./60% HR and stress conditions 40° C./75% HR, showing a fast drug release rate, more than 85% is delivered at first 15 minutes. The presence of MCC in extrusion-spheronization pellets does not retard or prolong drug release rate of API-001 in long term stability studies performed at 6 month.

Figure 4:
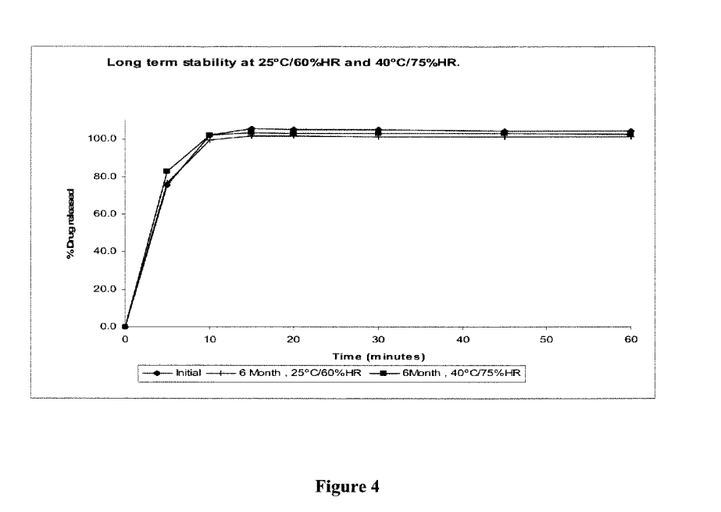
FIG. 4 represents a comparative in vitro release profile of extrusion-spheronization pellets of API-001, under the following conditions: paddle speed 50 rpm, medium HCl 0.1N pH 1.2, volume 900 ml (Sink conditions were maintained during all the study).

FIG. 4 represents a comparative in vitro release profile of extrusion-spheronization pellets of API-001 under the following conditions: paddle speed 50 rpm, medium HCl 0.1N pH 1.2, volume 900 ml (Sink conditions were maintained during all the study). In concrete, the tested formulation contained: 86.6% API-001, 2.9% PEG8000 as a binder and MCC 10.5% as a filler or aid for extrusion process.

The invention claimed is:

1. A pharmaceutical composition comprising (i)
   4-{2-[5-Methyl-1-(naphthalen-2-yl)-1H-pyrazol-3-yloxy]ethyl}morpholine hydrochloride,
   and (ii) pharmaceutically acceptable excipients,
   wherein said pharmaceutically acceptable excipients comprise polyethylene glycol (PEG) from 2.9% to 4.9% of the total dry weight of the pharmaceutical composition, and microcrystalline cellulose (MCC), such that the MCC/PEG weight ratio is 3.345 to 1.571, and
   with the proviso that the pharmaceutical composition does not contain carrageenan,
   wherein the compound (i) is present in an amount of at least 80% of the total dry weight of the pharmaceutical composition and the weight ratio of the compound to the pharmaceutically acceptable excipients is from 4:1 to 40:1.

2. The pharmaceutical composition according to claim 1, which further comprises an excipient selected from the group consisting of disintegrants, lubricants, plastizicers, and fillers.

3. The pharmaceutical composition according to claim 2, which is formulated for immediate release.

4. The pharmaceutical composition according to claim 1, which is comprised within a pharmaceutical dosage form selected from the group consisting of tablet, mini-tablet, powder, sachet, capsule, microsphere, matrix, ovule, suppository, wafer, pill, sprinkle, film, dry syrup, reconstitutable solid, gel, dispersion, solution, suspension, lozenge, troche, implant, triturate, platelet, or strip.

5. The pharmaceutical composition according to claim 1, wherein the polyethylene glycol has an average weight between 7000 and 9000.

6. A pharmaceutical composition in the form of a pellet comprising
   (i) 4-{2-[5-Methyl-1-(naphthalen-2-yl)-1H-pyrazol-3-yloxy]ethyl}morpholine hydrochloride, and
   (ii) pharmaceutically acceptable excipients,
   wherein the compound (i) is present in an amount of at least 80% of the total dry weight of the pharmaceutical composition,
   wherein said pharmaceutically acceptable excipients comprise polyethylene glycol (PEG) from 2.9% to 4.9% of the total dry weight of the pharmaceutical composition, and microcrystalline cellulose (MCC), such that the MCC/PEG weight ratio is 3.345 to 1.571, and
   wherein the pharmaceutical composition does not contain carrageenan.

7. The pharmaceutical composition according to claim 6, wherein the polyethylene glycol has an average weight between 7000 and 9000.

* * * * *